(12) United States Patent
Morris et al.

(10) Patent No.: US 8,394,447 B2
(45) Date of Patent: Mar. 12, 2013

(54) ABLUMINAL STENT COATING APPARATUS AND METHOD USING A BRUSH ASSEMBLY

(75) Inventors: Grayson Morris, San Francisco, CA (US); Svava Maria Atladottir, Mountain View, CA (US); Carla Pienknagura, San Carlos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 460 days.

(21) Appl. No.: 12/510,121

(22) Filed: Jul. 27, 2009

(65) Prior Publication Data
US 2009/0291196 A1 Nov. 26, 2009

Related U.S. Application Data

(62) Division of application No. 10/999,829, filed on Nov. 29, 2004, now Pat. No. 7,588,642.

(51) Int. Cl.
| | |
|---|---|
| *A61L 33/00* | (2006.01) |
| *B05D 3/12* | (2006.01) |
| *B05D 1/22* | (2006.01) |
| *C23C 16/52* | (2006.01) |
| *B05C 11/00* | (2006.01) |
| *A46B 11/02* | (2006.01) |

(52) U.S. Cl. ....... 427/2.24; 427/2.1; 427/2.25; 427/429; 401/268; 118/665; 118/669; 118/675; 118/713

(58) Field of Classification Search ............... 427/2.1, 427/2.24, 2.25, 8, 429; 118/668, 669, 675, 118/663, 665, 681, 712, 713; 15/21.1, 88.1, 15/88.2
See application file for complete search history.

(56) References Cited

U.S. PATENT DOCUMENTS

| | | | | |
|---|---|---|---|---|
| 2,244,952 A | * | 6/1941 | Kapelman | 222/387 |
| 3,860,987 A | * | 1/1975 | Bolli et al. | 15/29 |
| 4,279,527 A | * | 7/1981 | Moe et al. | 401/277 |
| 5,397,195 A | * | 3/1995 | Goncalves | 401/277 |
| 5,516,545 A | * | 5/1996 | Sandock | 427/96.9 |
| 5,738,728 A | * | 4/1998 | Tisone | 118/638 |
| 6,033,503 A | * | 3/2000 | Radowicz et al. | 156/64 |
| 6,056,993 A | | 5/2000 | Leidner et al. | |
| 6,068,202 A | * | 5/2000 | Hynes et al. | 239/290 |
| 6,375,459 B1 | | 4/2002 | Kamen et al. | |
| 6,395,326 B1 | * | 5/2002 | Castro et al. | 427/2.24 |
| 6,544,582 B1 | * | 4/2003 | Yoe | 427/2.24 |
| 6,641,320 B1 | * | 11/2003 | Ballot et al. | 401/206 |
| 7,204,110 B2 | | 4/2007 | Hammar et al. | |
| 2003/0157243 A1 | | 8/2003 | Trabold et al. | |
| 2003/0207019 A1 | * | 11/2003 | Shekalim et al. | 427/2.24 |
| 2003/0224320 A1 | * | 12/2003 | Kandelman et al. | 433/80 |
| 2004/0204750 A1 | * | 10/2004 | Dinh | 623/1.15 |
| 2005/0074544 A1 | * | 4/2005 | Pacetti et al. | 427/2.1 |

* cited by examiner

*Primary Examiner* — Timothy Meeks
*Assistant Examiner* — Cachet Sellman
(74) *Attorney, Agent, or Firm* — Squire Sanders (US) LLP (57) ABSTRACT

The apparatus and method use an optical feedback system to align a brush assembly with a stent strut. Once alignment is achieved, a coating is dispensed onto the stent strut via the brush assembly and the brush assembly is moved along the stent strut to coat the stent strut.

30 Claims, 5 Drawing Sheets

ABLUMINAL STENT COATING APPARATUS AND METHOD USING A BRUSH ASSEMBLY

CROSS-REFERENCE

This is a divisional of application Ser. No. 10/999,829, filed on Nov. 29, 2004, now U.S. Pat. No. 7,588,642, which is incorporated by reference as if fully set forth, including any figures, herein.

TECHNICAL FIELD

This invention relates generally to stent coating apparatuses, and more particularly, but not exclusively, provides a brush assembly and method for coating of an abluminal stent surface.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Figure 1:
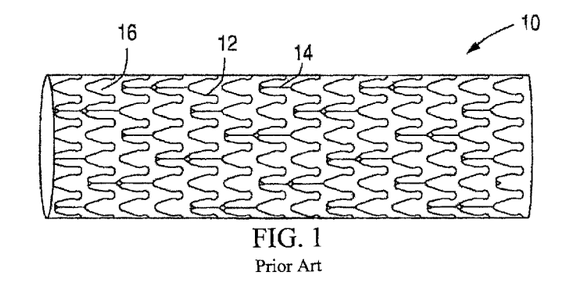
FIG. 1 is a diagram illustrating a conventional stent.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. The struts 12 and the connecting elements 14 define a tubular stent body having an outer, tissue-contacting surface and an inner surface.

Stents are being modified to provide drug delivery capabilities. A polymeric carrier, impregnated with a drug or therapeutic substance is coated on a stent. The conventional method of coating is by, for example, applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surfaces a coating of the polymer and the therapeutic substance impregnated in the polymer. The dipping or spraying of the composition onto the stent can result in a complete coverage of all stent surfaces, i.e., both luminal (inner) and abluminal (outer) surfaces, with a coating. However, having a coating on the luminal surface of the stent can have a detrimental impact on the stent's deliverability as well as the coating's mechanical integrity. Moreover, from a therapeutic standpoint, the therapeutic agents on an inner surface of the stent get washed away by the blood flow and typically can provide for an insignificant therapeutic effect. In contrast, the agents on the outer surfaces of the stent are in contact with the lumen, and provide for the delivery of the agent directly to the tissues. Polymers of a stent coating also elicit a response from the body. Reducing the amount to foreign material can only be beneficial.

Briefly, an inflatable balloon of a catheter assembly is inserted into a hollow bore of a coated stent. The stent is securely mounted on the balloon by a crimping process. The balloon is inflated to implant the stent, deflated, and then withdrawn out from the bore of the stent. A polymeric coating on the inner surface of the stent can increase the coefficient of friction between the stent and the balloon of a catheter assembly on which the stent is crimped for delivery. Additionally, some polymers have a "sticky" or "tacky" consistency. If the polymeric material either increases the coefficient of friction or adherers to the catheter balloon, the effective release of the stent from the balloon after deflation can be compromised. If the stent coating adheres to the balloon, the coating, or parts thereof, can be pulled off the stent during the process of deflation and withdrawal of the balloon following the placement of the stent. Adhesive, polymeric stent coatings can also experience extensive balloon sheer damage post-deployment, which could result in a thrombogenic stent surface and possible embolic debris. The stent coating can stretch when the balloon is expanded and may delaminate as a result of such shear stress.

Another shortcoming of the spray coating and immersion methods is that these methods tend to from defects on stents, such as webbing between adjacent stent struts 12 and connecting elements 14 and the pooling or clumping of coating on the struts 12 and/or connecting elements 14. In addition, spray coating can cause coating defects at the interface between a stent mandrel and the stent 10 as spray coating will coat both the stent 10 and the stent mandrel at this interface, possibly forming a clump. During removal of the stent 10 from the stent mandrel, this clump may detach from the stent 10, thereby leaving an uncoated surface on the stent 10. Alternatively, the clump may remain on the stent 10, thereby yielding a stent 10 with excessive coating.

Accordingly, a new apparatus and method are needed to enable selective coating of stent surfaces while minimizing the formation of defects.

SUMMARY

Embodiments of the invention provide an apparatus and method that enable selective coating of stent surfaces while avoiding coating defects caused by conventional spray coating and immersion coating techniques.

In an embodiment of the invention, that apparatus comprises a dispensing mechanism, a brush assembly in fluid communication with the dispensing mechanism, and an optical feedback system. The dispensing mechanism dispenses a coating onto the brush assembly and the optical feedback system aligns the brush assembly with a stent strut such that the brush assembly coats the stent strut with the dispensed coating.

It will be appreciated by one of ordinary skill in the art that the alignment can also be between the brush assembly and a connecting element in place of a stent strut. Accordingly, the use of the term strut or stent strut hereinafter also interchangeably refers to a connecting element.

In an embodiment of the invention, the method comprises: aligning a brush assembly with a stent strut, the brush assembly in fluid communication with a dispensing mechanism; and dispensing a coating from the dispensing mechanism onto the stent strut via the brush assembly.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 2:
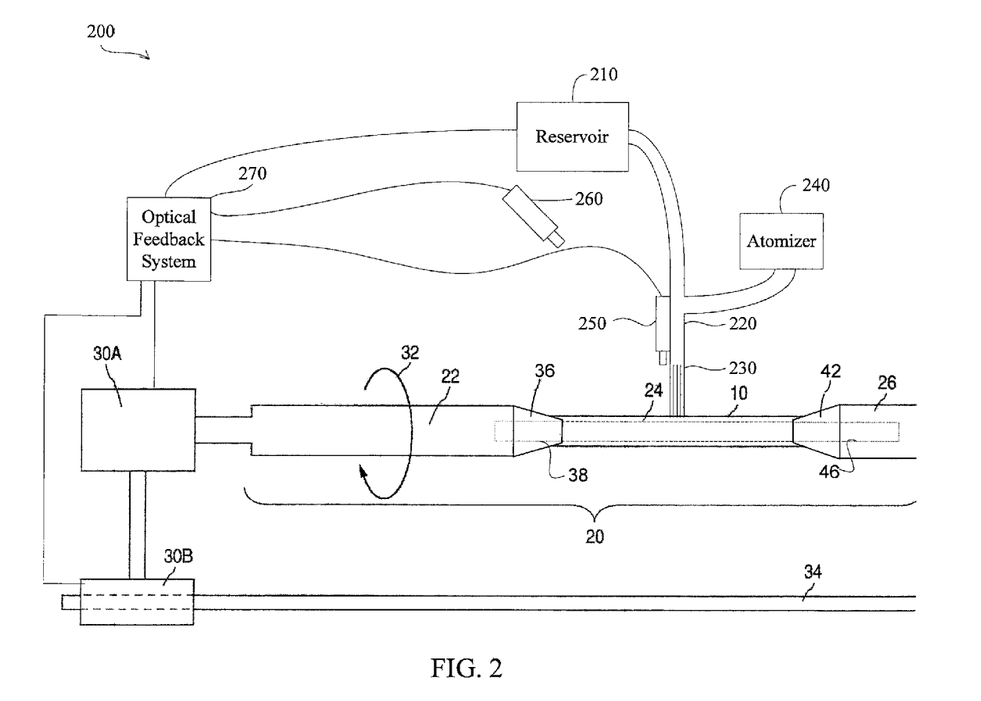
FIG. 2 is a block diagram illustrating a stent coating apparatus according to an embodiment of the invention.

FIG. 2 is a block diagram illustrating a stent coating apparatus 200 according to an embodiment of the invention. The apparatus 200, including a stent mandrel fixture 20 for supporting the stent 10, is illustrated to include a support member 22, a mandrel 24, and a lock member 26. The support member 22 can connect to a motor 30A so as to provide rotational motion about the longitudinal axis of the stent 10, as depicted by arrow 32, during a coating process. Another motor 30B can also be provided for moving the support member 22 in a linear direction, back and forth, along a rail 34.

The support member 22 includes a coning end portion 36, tapering inwardly. In accordance with one embodiment of the invention, the mandrel 24 can be permanently affixed to coning end portion 36. Alternatively, the support member 22 can include a bore 38 for receiving a first end of the mandrel 24. The first end of mandrel 24 can be threaded to screw into the bore 38 or, alternatively, can be retained within the bore 38 by a friction fit. The bore 38 should be deep enough so as to allow the mandrel 24 to securely mate with the support member 22. The depth of the bore 38 can also be overextended so as to allow a significant length of the mandrel 24 to penetrate or screw into the bore 38. The bore 38 can also extend completely through the support member 22. This would allow the length of the mandrel 24 to be adjusted to accommodate stents of various sizes.

The lock member 26 includes a coning end portion 42 tapering inwardly. A second end of the mandrel 24 can be permanently affixed to the lock member 26 if the first end is disengagable from the support member 22. Alternatively, in accordance with another embodiment, the mandrel 24 can have a threaded second end for screwing into a bore 46 of the lock member 26. The bore 46 can be of any suitable depth that would allow the lock member 26 to be incrementally moved closer to the support member 22. The bore 46 can also extend completely through the lock member 26. Accordingly, the stents 10 of any length can be securely pinched between the support and the lock members 22 and 26. In accordance with yet another embodiment, a non-threaded second end and the bore 46 combination is employed such that the second end can be press-fitted or friction-fitted within the bore 46 to prevent movement of the stent 10 on the stent mandrel fixture 20.

Positioned a distance from the stent 10 (e.g., above the stent 10) is a reservoir 210 holding a coating substance to be applied to the stent 10. The reservoir 210 is in fluid communication with a needle or other dispensing mechanism 220, which is in fluid communication with a brush assembly 230. In an embodiment of the invention, an atomizer 240 can be coupled to the needle 220 and provides atomizing air to the needle 220 for atomizing the coating substance before it is dispensed.

The reservoir 210 dispenses the coating substance to the needle 220, which dispenses it to the brush assembly 230, which will be discussed in further detail in conjunction with FIG. 4A-4F below. The reservoir 210 can dispense the coating substance using gravity and/or forced pressure (e.g., a pump). The use of forced pressure enables the accurate control of the amount of coating substance dispensed. The force must be high enough to allow for the adequate coating of the stent 10 but cannot to be too high such that it leads to non-uniform coating of the stent 10. The reservoir 210 can dispense the coating at a constant rate, at a variable rate, or intermittently. For example, during the application of the coating substance, the rate of coating dispensed can be adjusted so that certain sections of the stent 10 receive more coating than others. If the coating material is applied in an intermittent fashion, coating adjustments can be made during the stoppage of coating application. Further, the coating can be stopped while the brush assembly 230 is being repositioned relative to the stent 10. Negative pressure can be applied to the brush assembly 230 to prevent the coating from inadvertently dripping onto the stent 10.

The brush assembly 230 is aligned with a stent strut 12 and coats each individual stent strut 12. As will be discussed further below in conjunction with FIG. 5, coating flows from the needle 220 to and along the brush assembly 230 onto the stent strut 12, thereby limiting the coating to just the outer surface stent strut 12 and not other surfaces (e.g., the luminal surface) as in spaying and immersion techniques. In one embodiment, the sidewalls of the stent struts 12 between the outer and inner surfaces can be partially coated. Partial coating of sidewalls can be incidental, such as that some coating can flow from the outer surface onto the sidewalls. In some embodiments coating of sidewalls can be intentional, such that the brush is designed to deposit coating on the other surfaces. In some embodiment, the brush is designed to completely coat all of the sidewalls of the struts 12.

Coupled to the needle 220 can be a first imaging device 250 that images the stent 10 before and/or after the coating substance has been applied to a portion of the stent 10. The first imaging device 250, along with a second imaging device 260 located a distance from the stent 10, are both communicatively coupled to an optical feedback system 270 via wired or wireless techniques. The reservoir 210 and the atomizer 240 may also be communicatively coupled to the optical feedback system 270 via wired or wireless techniques. Based on the imagery provided by the imaging devices 250 and 260, the optical feedback system 270 controls movement of stent 10 via the motors 30A and 30B to keep the brush assembly 230 aligned with the stent struts 12 and recoat the stent struts 12 if improperly (or inadequately) coated.

During operation of the stent coating apparatus 200, the optical feedback system 270 causes the imaging device 260 to image the full surface of the stent 10 as the feedback system 270 causes the motor 30A to rotate the stent 10. After the initial imaging, the optical feedback system 270, using the imaging device 260, aligns the brush assembly 230 with a stent strut 12 by causing the engines 30A and 30B to rotate and translate the stent 10 until alignment is achieved. The optical feedback system 270 then causes the reservoir 210 (e.g., through a pump mechanism known to those of ordinary skill in the art) to dispense the coating substance through the needle 220 to the brush assembly 230. As the coating substance is dispensed, the optical feedback system 270 causes the engines 30A and 30B to rotate and translate the stent 10 in relation to the brush assembly 230 so as to effective drag the stent strut 12 along the brush assembly 230, thereby causing the strut 12 to be coated. In an embodiment of the invention, the optical feedback system 270 also cause the atomizer 240 to atomize the coating substance as it is being dispensed through the needle 220.

After a portion of the stent strut 12 has been coated, the optical feedback system 270 causes the reservoir 210 to cease dispensing the coating substance and causes the imaging device 250 to image the stent strut 12 to determine if the strut 12 has been adequately coated. This determination can be made by measuring the difference in color and/or reflectivity of the stent strut 12 before and after the coating process. If the strut 12 has been adequately coated, then the optical feedback system 270 causes the engines 30A and 30B to rotate and translate the stent 10 so that the brush assembly 230 is aligned with an uncoated stent 10 section and the above process is then repeated. If the stent strut 12 is not coated adequately, then the optical feedback system 270 causes the engines 30A and 30B to rotate and translate the stent 10 and the reservoir 210 to dispense the coating substance to recoat the stent strut 12. In another embodiment of the invention, the optical feedback system 270 can cause checking and recoating of the stent 10 after the entire stent 10 is goes through a first coating pass.

In an embodiment of the invention, the imaging devices 250 and 260 include charge coupled devices (CCDs) or complementary metal oxide semiconductor (CMOS) devices. In an embodiment of the invention, the imaging devices 250 and 260 are combined into a single imaging device. Further, it will be appreciated by one of ordinary skill in the art that placement of the imaging devices 250 and 260 can vary as long as they have an acceptable view of the stent 10. In addition, one of ordinary skill in the art will realize that the stent mandrel fixture 20 can take any form or shape as long as it is capable of securely holding the stent 10 in place.

Accordingly, embodiments of the invention enable the fine coating of specific surfaces of the stent 10, thereby avoiding coating defects that can occur with spray coating and immersion coating methods and limiting the coating to only the abluminal surface and/or sidewalls of the stent 10. Application of the coating in the gaps 16 between the stent struts 12 can be partially, or preferable completely, avoided.

After the brush coating of the stent 10 abluminal surface, the stent 10 can then have the inner surface coated via electroplating or spray coating. Without masking the outer surface of the stent 10, both electroplating and spray coating may yield some composition onto the outer surface and sidewalls of the stent 10. However, the inner surface would be substantially solely coated with a single composition different from the composition used to coat the outer surface of the stent 10. Accordingly, it will be appreciated by one of ordinary skill in the art that this embodiment enables the coating of the inner surface and the outer surface of the stent 10 with different compositions. For example, the inner surface could be coated with a composition having a bio-beneficial therapeutic substance for delivery downstream of the stent 10 (e.g., an anticoagulant, such as heparin, to reduce platelet aggregation, clotting and thrombus formation) while the outer surface of the stent 10 could be coating with a composition having a therapeutic substance for local delivery to a blood vessel wall (e.g., an anti-inflammatory drug to treat vessel wall inflammation or a drug for the treatment of restenosis).

The components of the coating substance or composition can include a solvent or a solvent system comprising multiple solvents, a polymer or a combination of polymers, a therapeutic substance or a drug or a combination of drugs. In some embodiments, the coating substance can be exclusively a polymer or a combination of polymers (e.g., for application of a primer layer or topcoat layer). In some embodiments, the coating substance can be a drug that is polymer free. Polymers can be biostable, bioabsorbable, biodegradable, or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

Representative examples of polymers that may be used include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(D-lactic acid), poly(D-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Representative examples of polymers that may be especially well suited for use include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

"Solvent" is defined as a liquid substance or composition that is compatible with the polymer and/or drug and is capable of dissolving the polymer and/or drug at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof.

The therapeutic substance or drug can include any substance capable of exerting a therapeutic or prophylactic effect. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy) propyl-rapamycin, 40-O-[2-(2-hydroxy)ethoxy]ethyl-rapamycin, and 40-O-tetrazole-rapamycin.

Figure 3:
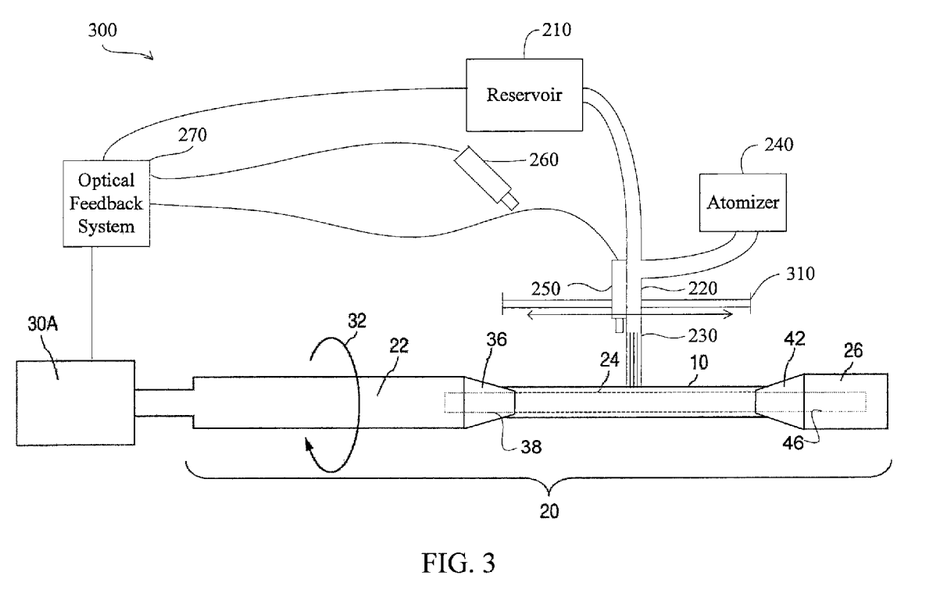
FIG. 3 is a block diagram illustrating a stent coating apparatus according to another embodiment of the invention.

FIG. 3 is a block diagram illustrating a stent coating apparatus 300 according to another embodiment of the invention. The stent coating apparatus 300 is similar to the stent coating apparatus 200. However, the brush assembly 230 is capable of translational movement along a guide rail 310. Accordingly, the alignment of the brush assembly 230 with a stent strut 12 is accomplished by the optical feedback system 270 causing the engine 30A to rotate the stent 10 in combination with causing the brush assembly 230 to move along the guard rail 310. The guard rail 310 should be at least about as long as the stent 10 to enable the brush assembly 230 full mobility over the length of the stent 10. In some embodiments, the brush assembly 230 is capable of translational movement along the guide rail 310 in combination with rotation and translation of the stent 10.

In another embodiment of the invention, the brush assembly 230 is coupled to a painting robot, such as one have six axes (three for the base motions and three for applicator orientation) that incorporates machine vision and is electrically driven. Accordingly, the brush assembly 230 can fully rotate around and translate along a stent 10 in a stationary position. Alternatively, both the brush assembly 230 and the stent 10 can rotate and/or translate. For example, the brush assembly 230 can move for alignment with a strut of the stent 10 while the stent 10 can move during coating after alignment, vice versa, or a combination of both.

In any of the above-mentioned embodiments, the coating process can be continuous, i.e., the brush assembly 230 can move along and coat the entire stent 10 without lifting off of the stent, or move intermittently, i.e., coating a first section of the stent 10, optionally lifting off and then aligning with a second section of the stent 10, and coating that second section. The second section may be adjacent to the first section or located a distance from the first section.

FIG. 4A, FIG. 4B, FIG. 4C, FIG. 4D, FIG. 4E, and FIG. 4F are diagrams illustrating the brush assemblies 230a-230d of the stent coating apparatuses 200 and 300 according to embodiments of the invention. The brush assembly 230a of FIG. 4A can be coupled to a brush module 400 that can be coupled to a mouth of the needle 220. The brush module 400 comprises a spongy or porous material that enables a coating substance to travel through the module 400 (e.g., a mesh plate) onto the brush assembly 230a. The brush assembly 230a comprises a plurality of fibers or bristles made of any suitable material that enables the flow of the coating substance. In an embodiment of the invention, the bristles can be made from polymer (e.g., rubber), glass, pig bristle, metal fibers, ultra-fine non-absorbent or absorbent fibers, etc. The fibers of the brush assembly 230a can be coupled to the module 400 by stringing the fibers through the pores of the module 400. In another embodiment of the invention, the fibers can be inserted directly into the mouth of the needle 220 without a module 400 and the mouth of the needle 220 is then mechanically compressed to hold the fibers in place. Any component including the needle 220, brush module 400 and brush assembly 230 can be disposable so as to allow a user to use different materials, for example for construction of a tri-layer coating such that at least two of the primer, drug/polymer, and topcoat layers are made from different materials.

Figure 4A:
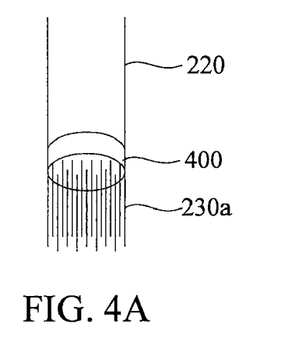
FIG. 4A, FIG. 4B, FIG. 4C, FIG. 4D, FIG. 4E, and FIG. 4F are diagrams illustrating brush assemblies of the stent coating apparatuses according to embodiments of the invention.
Figure 4B:
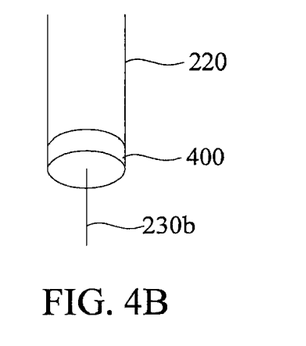

The number of fibers in the brush assembly 230a can vary from a single fiber (e.g., the brush assembly 230b having a single fiber centered in the mouth of the needle 220) to a plurality of fibers (e.g., hundreds). The lengths of the fibers vary based on the length of the stent strut 12. The length, number, and fiber material also vary based on the viscosity of the coating substance, the rate of application, the pattern of the stent, among other factors. The fibers can be long enough such that during the brush process, the fibers can drag along the surface being coated. Alternatively, the fibers can be short enough so as to be less pliable to prevent bending or dragging the fibers. A combination of the two embodiments can also be used. For example, the fibers on opposing edges can be long enough to drag on the sidewalls while the fibers on the middle segment are thicker or made from more rigid material so as to prevent dragging of the fibers during the application process. Alternatively, the fibers of middle segment can be more pliant while the fibers at the opposing edges can be rigid.

In an embodiment of the invention, fiber length varies from about ⅛ inch to about 1 inch. In one embodiment, the fiber diameter is about 0.004 inches. As shown in FIG. 4D-FIG. 4F, the length of the fibers in the brush assembly 230d can vary from each other. Accordingly, when the needle 220 is aligned with stent strut 12, longer fibers extend down the sidewalls of the stent strut 12 while shorter fibers extend along the outside surface of the stent strut 12, thereby enabling coating of both the outer surface and the sidewalls of the stent strut 12. For example, as shown in FIG. 4E, a cross section of the needle 220 with brush assembly 230d is shown. The lengths of the fibers are represented by their diameter and as such, fibers aligned with the sidewalls of the strut 12 are longer than fibers aligned with the abluminal surface of the strut 12. (The diameters of the fibers in FIG. 4E do not represent the relative width of the fibers although in some embodiments, widths of the fibers can be different).

Referring in more detail to FIGS. 4E and 4F, as best illustrated, the area populated by shorter fibers of the middle portion of the brush assembly 230d are bounded by the longer fibers at two of the end regions of the brush assembly 230d, which in effect provides a passageway or channel through the brush assembly 230d. The width of this channel can be designed so as to be equivalent or generally equivalent to the width of a strut being coating. Accordingly, during the coating process, a strut fits between the longer fibers as the brush is guided across the strut. With interchangeable components, a user can select a brush that is compatible with a width of a given strut.

Figure 4C:
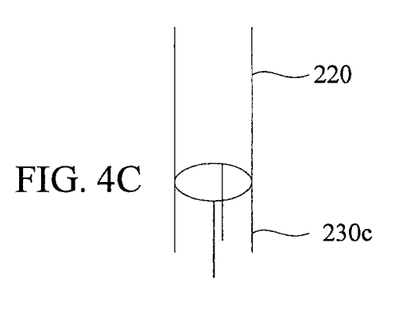
Figure 4D:
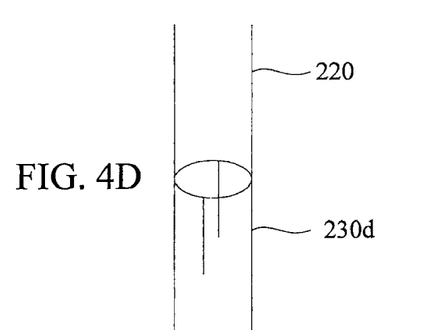
Figure 4E:
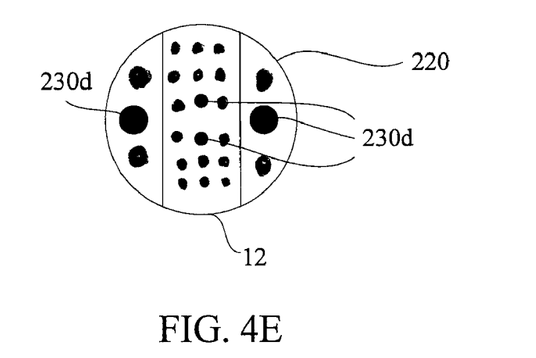
Figure 4F:
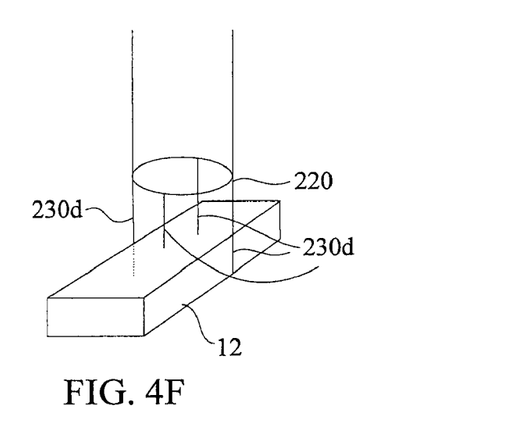

As shown in FIG. 4C and FIG. 4D, embodiments of the invention can include brush assemblies 230c and 230d wherein fibers of the assemblies are solely attached to perimeter (circumference) of the needle 220 mouth. Accordingly, the module 400 is not required. In an embodiment of the invention, a brush assembly can include fibers coupled to both a module 400 and to the perimeter of the needle 220 mouth.

Figure 5:
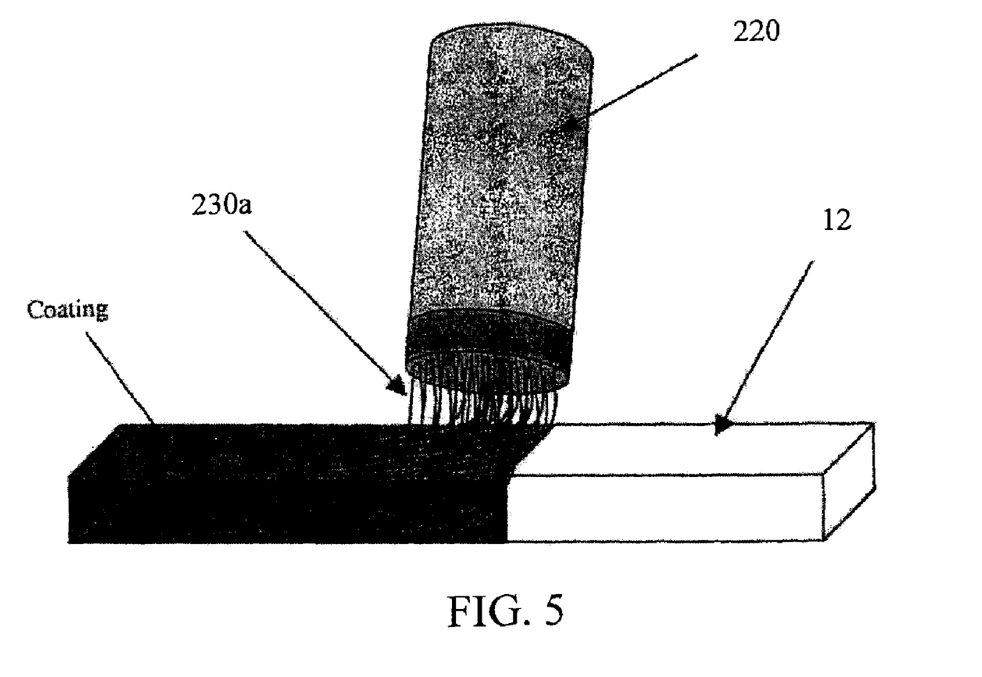
FIG. 5 is a diagram illustrating a brush assembly coating a stent strut.

FIG. 5 is a diagram illustrating the brush assembly 230a coating a stent strut 12. During operation of the system 200 or 300, the optical feedback system 270 causes the alignment of the needle 220 with a stent strut 12. The optical feedback system 270 then causes the reservoir 210 to dispense a coating substance to the needle 220 to the brush assembly 230a. In addition, the optical feedback system 270 can also cause the atomizer 240 to supply atomizing air to the needle 220 during dispensing of the coating substance.

In an embodiment of the invention, the brush assembly 230a is aligned with the stent strut 12 such that fibers of the brush assembly 230a extend along the full depth of the sidewalls of the strut 12, thereby enabling coating of the stent strut 12 abluminal surface as well as the sidewalls. In another embodiment of the invention, the needle 220 is positioned so that the fibers of the brush assembly 230a only extend to the abluminal surface of the stent strut 12, thereby coating only the abluminal stent strut 12 surface and not the sidewalls of the stent strut 12.

Further, as can be seen in FIG. 5, the coating can produce a different color on the stent strut 12, thereby enabling the optical feedback system 270 to determine if the strut 12 has not been adequately coated based on a color change. In an alternative embodiment of the invention, the optical feedback system 270 can measure a change in reflectivity of the stent strut 12 and/or other parameters.

Figure 6:
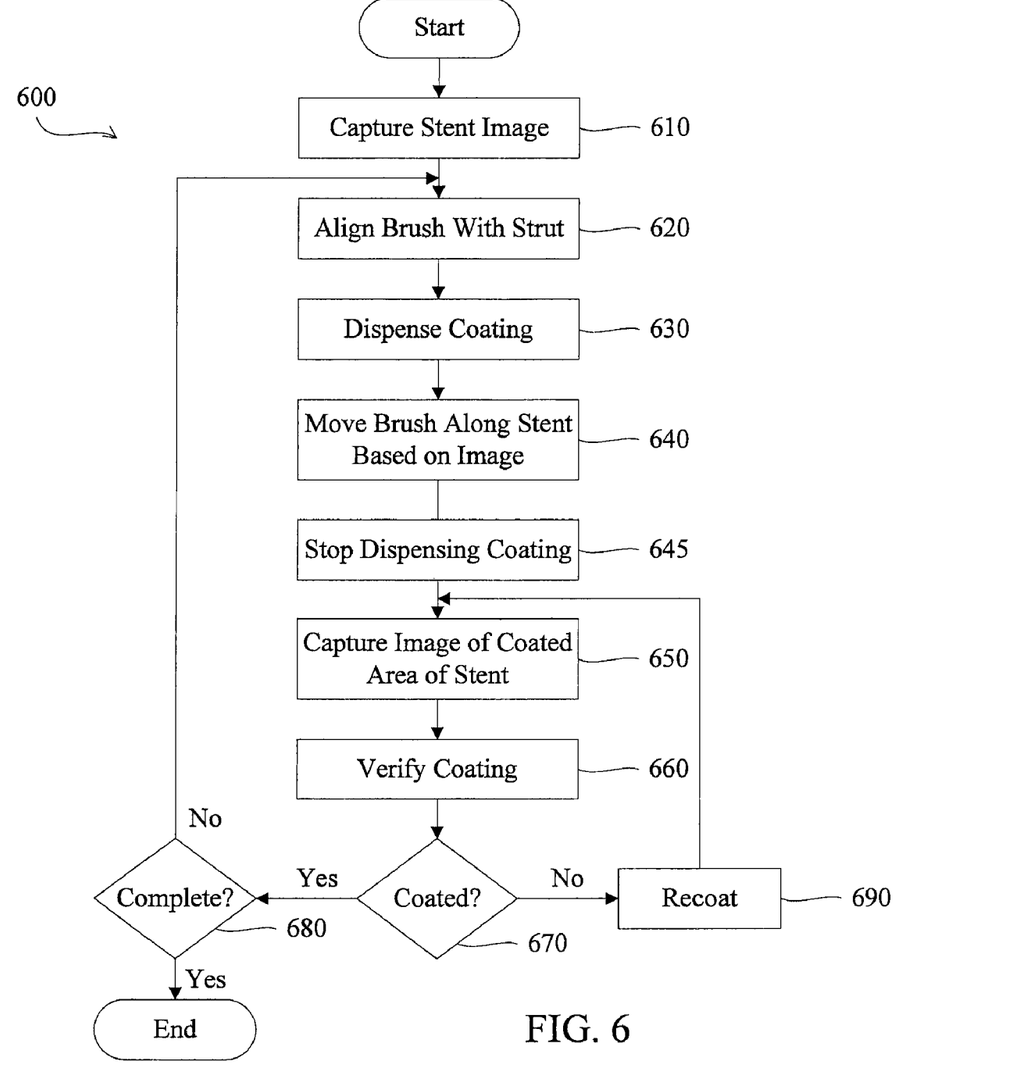
FIG. 6 is a flowchart illustrating a method of coating an abluminal stent surface.

FIG. 6 is a flowchart illustrating a method 600 of coating an abluminal stent surface. In an embodiment of the invention, the system 200 or 300 can implement the method 600. First, an image of the stent 10 is captured (610) as the stent 10 is rotated. Based on the captured image, a brush is aligned (620) with a stent strut 12 of the stent 10 via rotation and/or translation of the stent 10 and/or translation of the brush. A coating is then dispensed (630) onto the brush. In an embodiment of the invention, during the dispensing (630), the coating can also be atomized. As the coating is being dispensed (630), the brush and/or stent are moved (640) relative to each other so as to coat at least a portion of the stent strut 12.

The dispensing is then stopped (645), and an image of at least a portion of the stent that was just coated in captured (650). Using the captured image, the coating is verified (660) based on color change, reflectivity change, and/or other parameters. If (670) the coating is not verified (e.g., the stent strut 12 was not fully coated), then the strut 12 is recoated (690) by realigning the brush with the strut 12, dispensing the coating, and moving the brush relative to the strut. Capturing (650) an image and verifying (660) are then repeated.

If (670) the coating is verified and if (680) the stent has been completely coated, then the method 600 ends. Otherwise, the method 600 is repeated with a different stent strut starting with the aligned (620).

In an embodiment of the invention, the luminal surface of the stent 10 can then be coating with a different coating using electroplating or other technique. Accordingly, the abluminal surface and the luminal surface can coated with different coatings.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating a stent, comprising:
   aligning a brush assembly with a strut of a stent, the brush assembly in fluid communication with a dispensing mechanism; and
   dispensing a coating from the dispensing mechanism onto the stent via the brush assembly,
   wherein the brush assembly includes a plurality of fibers, and the dispensing mechanism includes a dispensing needle having a mouth coupled to the fibers.

2. The method of claim 1, further comprising moving the brush assembly and the stent relative to each other while the coating is being dispensed.

3. The method of claim 1, further comprising
   verifying the coating on the stent and
   recoating of the strut if the coating is determined to be inadequate.

4. The method of claim 3, wherein the coating is verified by an imaging device by measuring the difference in color and/or reflectivity of the stent before and after the coating process.

5. The method of claim 3, comprising a first imaging device for aligning the brush assembly with the strut of the stent and a second imaging device for verifying the coating on the stent.

6. The method of claim 1, wherein the brush assembly comprises fibers of different lengths.

7. The method of claim 1, wherein a porous module couples the mouth of the needle to the fibers of the brush assembly.

8. The method of claim 1, wherein the brush assembly includes at least one fiber fixed to a perimeter of the mouth.

9. The method of claim 1, wherein the aligning aligns the brush assembly with the stent strut such that both an abluminal surface and sidewalls of the stent strut are coated.

10. The method of claim 1, wherein the aligning aligns the brush assembly with the stent strut such that only the abluminal surface of the stent strut is coated.

11. The method of claim 1, wherein the aligning aligns the brush assembly with the stent strut via rotation and translation of the stent.

12. The method of claim 1, wherein the aligning aligns the brush assembly with the stent strut via rotation of the stent and translation of dispensing mechanism.

13. A method of coating a stent, comprising:
   aligning a brush assembly with a strut of a stent, the brush assembly in fluid communication with a dispensing mechanism; and
   dispensing a coating from the dispensing mechanism onto the stent via the brush assembly,
   wherein the brush assembly comprises an area populated by shorter fibers in the middle portion of the brush assembly bounded by longer fibers at two of the end regions of the brush assembly such that a channel is formed through the brush assembly, wherein the width of the channel is equivalent or generally equivalent to the width of the stent strut.

14. The method of claim 13, wherein the fibers of the middle portion are more pliable than the fibers at the two end regions.

15. The method of claim 13, wherein the fibers of the middle portion are more ridged than the fibers at the two end regions.

16. The method of claim 1, wherein the brush assembly comprises fibers of different degrees of pliability to allow for even coating application on the stent.

17. The method of claim 1, wherein the coating is dispensed at a variable rate such that certain sections of the stent receive more coating than others.

18. The method of claim 1, further comprising terminating dispensing of the coating onto the stent, followed by realignment of the brush assembly relative to the stent, and followed by dispensing the coating onto the stent.

19. The method of claim 1, further comprising applying negative pressure to the brush assembly to prevent the coating from inadvertently dripping onto the stent.

20. The method of claim 1, further comprising atomizing the coating as the coating is being dispensed from the needle.

21. A method of coating a stent, comprising
   imaging a full surface of a stent by an imaging device;
   providing data based on the imaging to an optical feedback system;
   aligning a brush assembly, in communication with the optical feedback system, with the stent based on operation of the optical feedback system;
   dispensing a coating composition from a needle to the brush assembly;
   atomizing the coating composition as the coating composition is being dispensed from the needle;
   dispensing the coating composition on the stent from the brush assembly;
   ceasing the dispensing of the coating composition on the stent; and
   imaging the stent to determine if a coating characteristic meets a coating parameter.

22. The method of claim 21, wherein only a partial section of the stent is coated and (1) if the coating characteristic meets the coating parameter, the method additionally includes aligning the brush assembly with an uncoated section of the stent and dispensing the coating composition on the uncoated section of the stent; or (2) if the coating characteristic does not meet the coating parameter, the section of the stent that is intended to be coated is re-coated until the coating characteristic meets the coating parameter.

23. The method of claim 21, wherein the entire stent goes through a coating pass, followed by the act of imaging the stent to determine if the coating characteristic meets the coating parameter.

24. The method of claim 21, wherein the ceasing of dispensing of the coating composition on the stent comprises applying negative pressure to the brush assembly to prevent any coating composition from discharging out from the brush assembly.

25. The method of claim 21, wherein for alignment and during dispensing the stent moves rotationally and the brush assembly moves linearly.

26. The method of claim 21, wherein imaging the full surface of the stent by an imaging device comprising causing the stent to rotate under the imaging device with the use of a motor.

27. The method of claim 21, wherein the imaging of the stent to determine if a coating characteristic meets a coating parameter is conducted by a second imaging device, different than the imaging device used for imaging the full surface of the stent.

28. The method of claim 21, wherein the dispensing of the coating composition on the stent by the brush assembly comprises coating a first section of the stent, followed by:
   the ceasing of dispensing of the coating composition on the stent;
   lifting off of the brush assembly;
   aligning the brush assembly with a second section of the stent; and
   dispensing the coating composition on the second section of the stent by the brush assembly.

29. The method of claim 28, wherein the first section is adjacent to the second section.

30. The method of claim 28, wherein the second section is positioned at a distance away from the first section.

* * * * *